(12) United States Patent
Iketani et al.

(10) Patent No.: US 7,857,751 B2
(45) Date of Patent: Dec. 28, 2010

(54) ELECTRONIC ENDOSCOPE SYSTEM INCLUDING IMAGE SYNTHESIZING PROCESSOR

(75) Inventors: Kohei Iketani, Saitama (JP); Mitsufumi Fukuyama, Hyogo (JP)

(73) Assignee: Hoya Corporation, Tokyo (JP)

( * ) Notice: Subject to any disclaimer, the term of this patent is extended or adjusted under 35 U.S.C. 154(b) by 1143 days.

(21) Appl. No.: 11/530,624

(22) Filed: Sep. 11, 2006

(65) Prior Publication Data

US 2007/0073104 A1 Mar. 29, 2007

(30) Foreign Application Priority Data

Sep. 12, 2005 (JP) ............... P2005-263942

(51) Int. Cl.
*A61B 1/04* (2006.01)
(52) U.S. Cl. ............... 600/109; 600/118; 600/160
(58) Field of Classification Search ............ 600/160, 600/109, 118, 178; 348/65, 71, 76
See application file for complete search history.

(56) References Cited

U.S. PATENT DOCUMENTS

| | | | |
|---|---|---|---|
| 6,371,908 B1 * | 4/2002 | Furusawa et al. | 600/160 |
| 6,960,165 B2 | 11/2005 | Ueno et al. | |
| 7,179,222 B2 * | 2/2007 | Imaizumi et al. | 600/109 |
| 7,204,803 B2 * | 4/2007 | Ueno et al. | 600/109 |
| 7,632,227 B2 * | 12/2009 | Sugimoto et al. | 600/160 |
| 2002/0022766 A1 * | 2/2002 | Adachi | 600/160 |
| 2002/0026098 A1 * | 2/2002 | Kobayashi | 600/160 |
| 2002/0093563 A1 * | 7/2002 | Cline et al. | 348/65 |
| 2003/0007087 A1 * | 1/2003 | Hakamata et al. | 348/370 |
| 2006/0178565 A1 * | 8/2006 | Matsui et al. | 600/160 |
| 2006/0256191 A1 | 11/2006 | Iketani et al. | |
| 2007/0015963 A1 * | 1/2007 | Fengler et al. | 600/109 |

FOREIGN PATENT DOCUMENTS

JP 2003-126014 5/2003
JP 2003-290130 10/2003

OTHER PUBLICATIONS

English language Abstract of JP 2003-290130.

* cited by examiner

*Primary Examiner*—John P Leubecker
(74) *Attorney, Agent, or Firm*—Greenblum & Bernstein P.L.C.

(57) ABSTRACT

An electronic endoscope system has a video-scope, an illumination apparatus, an imaging device, and an image synthesizing processor. The illumination apparatus illuminates a normal light and an excitation-light from the video-scope onto an object. The normal light is reflected off the object, and the excitation-light causes the object to emit fluorescence. The imaging device on the video-scope captures a normal image that is formed by the reflected normal light and a fluorescent image that is formed by the fluorescence. The image synthesizing processor synthesizes the normal image and the fluorescent image into a synthesized image. A color signal of the synthesized image is the same as a color signal of the normal image. A luminance signal or the synthesized image is obtained by mixing a luminance signal of the normal image and a luminance signal of the fluorescent image in a predetermined proportion.

14 Claims, 7 Drawing Sheets

ELECTRONIC ENDOSCOPE SYSTEM INCLUDING IMAGE SYNTHESIZING PROCESSOR

BACKGROUND OF THE INVENTION

1. Field of the Invention

The present invention relates to an electronic endoscope system that is capable of identifying an abnormal tissue, such as cancer in an organ, using auto-fluorescence emitted from the tissue onto which the excitation light is illuminated.

2. Description of the Related Art

A tissue in the organ, which the excitation light having a wavelength in the ultraviolet range or in that vicinity is illuminated onto, enters into an excited state so as to emit auto-fluorescence. The intensity of the auto-fluorescence from abnormal tissue (for example, cancer) is weaker than that of normal tissue. Therefore, it is known that the auto-fluorescent endoscope system identifies the abnormal tissue, based on the auto-fluorescent image that is formed from the auto-fluorescence.

Incidentally, the lumen (interior hollow area) in the organ does not emit the auto-fluorescence, so the intensity of the auto-fluorescence in the lumen is weak, similarly to with the abnormal tissue. Thus, the abnormal tissue is not distinguished from the lumen by only the auto-fluorescent image. Accordingly, in the auto fluorescent endoscope system, the normal image that is obtained when the white light is illuminated onto the tissue is also referred to in order to identify the abnormal tissue.

The lumen is dark in the normal image because it cannot reflect white light, but the abnormal tissue is bright in the normal image because it can reflect white light. Therefore, the part that is dark in the fluorescent image but that is bright in the normal image is identified as the abnormal tissue.

Conventionally, the normal image and the fluorescent image are arranged right to left on the same monitor, so that in a user can identify the abnormal tissue optically using both images simultaneously displaying on the monitor. However, with this method, it is difficult to identify the abnormal tissue because the image displaying area for each image is small. Further, this method requires that the identification of the abnormal tissue depend on the doctor's divination and experience. Therefore, there is a fear of a doctor with insufficient experience missing out on identifying the abnormal tissue.

Therefore, recently improved auto-fluorescent endoscope systems have been developed, as described below. For example, the abnormal tissue is automatically identified based on both the luminance values of the normal image and the luminance values of the fluorescent image, and the pseudo-color (yellow or red, for example) overlaps onto the area corresponding to the abnormal tissue, as shown in Japanese Unexamined Patent Publication (KOKAI) No. 2003-290130. Due to this method, it is easy to identify the abnormal tissue even if the doctor does not have much experience.

However, it is impossible to observe the tissue itself corresponding to the area where the pseudo-color overlaps with this method. Further, if a part of the tissue bleeds, the bleeding part may be misidentified as abnormal tissue, so that the pseudo-color overlaps onto the bleeding part, because the luminance value of the bleeding part can be low in the fluorescent image but can be high in the normal image, similarly to with the abnormal tissue.

As shown in Japanese Unexamined Patent Publication (KOKAI) No. 2003-126014, the fluorescent image signals corresponding to the fluorescent image are generated by illuminating the excitation light onto the tissue, and two kinds of normal image signals are obtained when the different color lights are illuminated onto the tissue, respectively. A pseudo-color display image is generated based on two kind of normal image signals and the fluorescent image signals, so as to identify the normal tissue by the first pseudo-color and the abnormal tissue by the second pseudo-color. However, the pseudo-color display image does not express the tissue by its natural color; therefore, it interferes with correct observation of the tissue.

SUMMARY OF THE INVENTION

Therefore, an object of the present invention is to provide an electronic endoscope system that is capable of indicating the abnormal tissue that is distinguished from the normal tissue without using a different color from the natural color of the tissue.

According to the present invention, there is provided an electronic endoscope system that comprises a video-scope, an illumination apparatus, an imaging device, and an image synthesizing processor.

The illumination apparatus illuminates a normal light and an excitation-light from the video-scope onto an object. The normal light is reflected off the object, and the excitation-light causes the object to enter into an excited state, so that the object emits fluorescence. The imaging device is provided on the video-scope, and receives the reflected normal light and the fluorescence so as to capture a normal image and a fluorescent image, respectively. The image synthesizing processor synthesizes the normal image and the fluorescent image into a synthesized image. The color signals of the synthesized image are the same as the color signals of the normal image. The luminance signals of the synthesized image are obtained by mixing the luminance signals of the normal image and the luminance signals of the fluorescent image in a predetermined proportion.

The electronic endoscope system can comprise a gain adjustment processor that adjusts a gain of a luminance signal of at least one of the normal image and the fluorescent image, so that the luminance level of the normal image coincides with that of the fluorescent image. In this case, the luminance level of the synthesized image is preferably kept to the coinciding luminance level.

The gain adjustment processor preferably adjusts the gain of the luminance signal, so that the average of the luminance value of the normal image coincides with the average of the luminance value of the fluorescent image.

The illumination apparatus may illuminate the normal light in a predetermined period, and the excitation-light in another predetermined period. The imaging device may also capture the normal image in the predetermined period, and the fluorescent image in another predetermined period.

For example, the illumination apparatus alternately illuminates either the normal light or the excitation-light in each of two regular periods that continue interleavingly, so that the imaging device captures either the normal image or the fluorescent image alternately in each of two regular periods. The image synthesizing processor preferably synthesizes the normal image that is captured in one regular period of the two regular periods and the fluorescent image that is captured in the succeeding or the preceding period of the one regular period. The regulars period can be a one-field period, for example.

Optionally, normal image signals corresponding to the normal image that are captured in the one regular period are input to the image synthesizing processor not only in the one regular period, but also in a succeeding regular period of the one regular period. Similarly, fluorescent image signals corresponding to the fluorescent image that are captured in the other regular period of two regular periods are input to the image synthesizing processor not only in the other period, but also in a succeeding period of the other period. In this case, the image synthesizing processor synthesizes the normal image signals and fluorescent image signals which are input thereto in the same regular period. The predetermined proportion is preferably set by an input switch.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
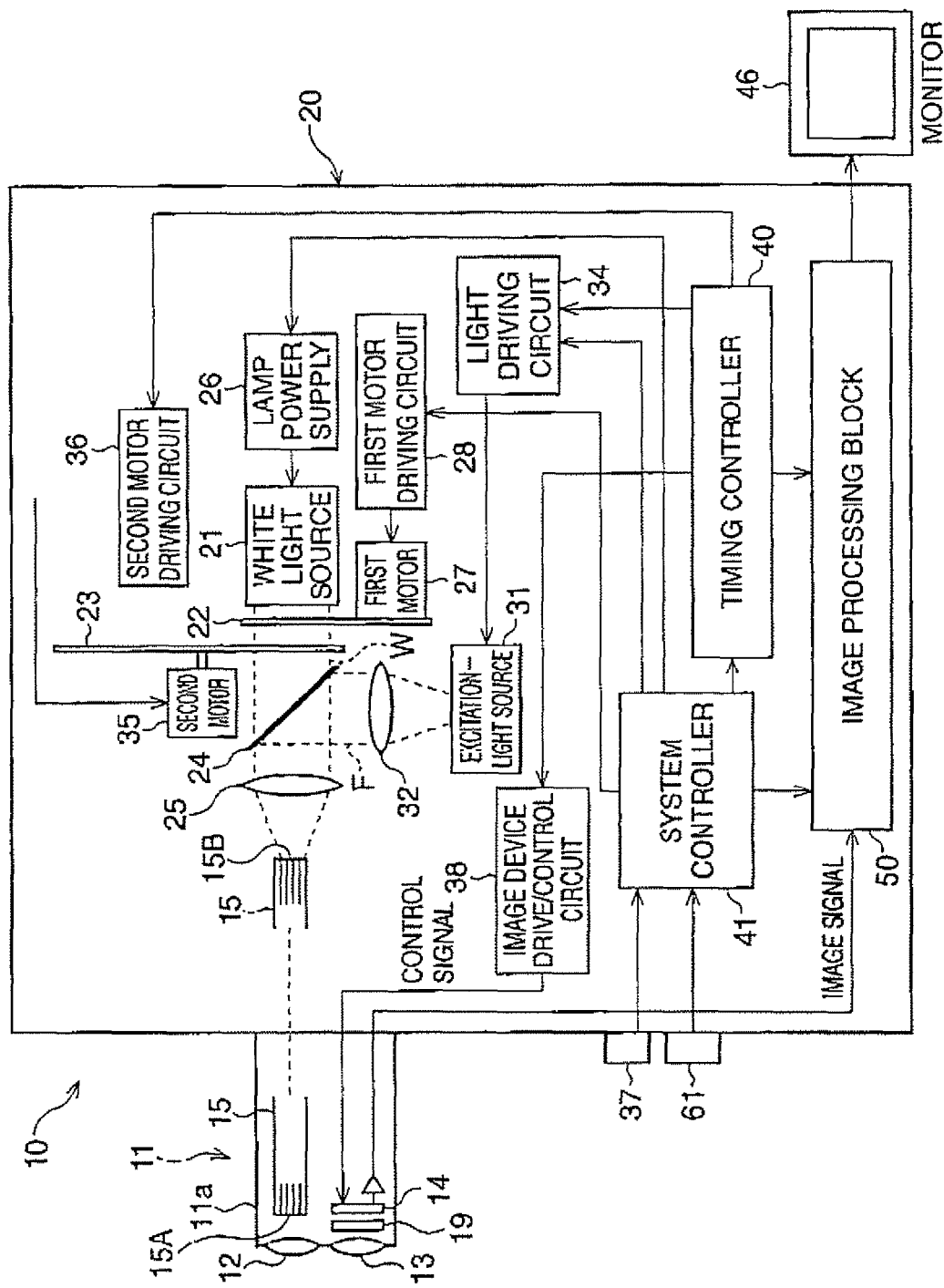
FIG. 1 is block diagram of an electronic endoscope system.

The present invention will be described below with reference to the embodiments shown in the drawings.

FIG. 1 is a block diagram of an electronic endoscope system. The electronic endoscope system 10 has a video-processor 20, a video-scope 11, and a monitor 46, which are connected to the video-processor 20.

The video-scope 11, which is inserted into a body for observing a tissue in an organ, can be attached to or removed from the video-processor 20. The video-scope 11 has a diffusion lens 12, an objective lens 13, a light guide 15, an excitation-light cut filter 19, and an imaging device 14. The diffusion lens 12 and the objective lens 13 are disposed on a tip portion 11a of the video-scope 11. The excitation-light cut filter 19 and the imaging device 14 are disposed in this sequence on the back of the objective lens 13 on the optical axis of the objective lens 13. The light guide 15 is inserted into the video-scope 11. An output end 15A of the light guide 15 is disposed on the back of the diffusion lens 12 on the optical axis of the diffusion lens 12, and an incident end 15B oaf the light guide 15 is disposed in the video-processor 20.

The video-processor 20 has a timing controller 40 and a system controller 41. The system controller 41 controls the entirety of the electronic endoscope system 10, including the tinting controller 40.

The video-processor 20 has a white light source 21 (for example, a xenon lamp) that emits the white light W (the normal light), and an excitation-light source 31 (for example, a laser light source) that emits the excitation-light F. The lamp power supply 26 applies the voltage to the white light source 21, so that the white light source 21 emits the white light W.

The white light W passes from right to left in FIG. 1 through a diaphragm 22, a rotary shutter 23, and a dichroic mirror 24 so as to be incident to the condensing lens 25. The excitation-light F, which emits from the excitation-light source 31 from bottom to up in FIG. 1 as the diffusing light, is collimated to a parallel light by a collimate lens 32. The (parallel) excitation-light F, which is reflected by the dichroic mirror 24, passes from right to left in FIG. 1, similarly to the white light W, so as to be incident to the condensing lens 25. The white or excitation-light W or F, respectively, which is condensed by the condensing lens 25, is incident to the light guide 15 at the incident end 15B.

Whether the white light W emits from the white light source 21 is controlled by the voltage applied to the white light source 21. The quantity of white light W that is emitted by the white light source 21 is controlled by the diaphragm 22, which is adjusted by a first motor 27. The first motor 27 is driven by a first motor driving circuit 28.

Figure 2:
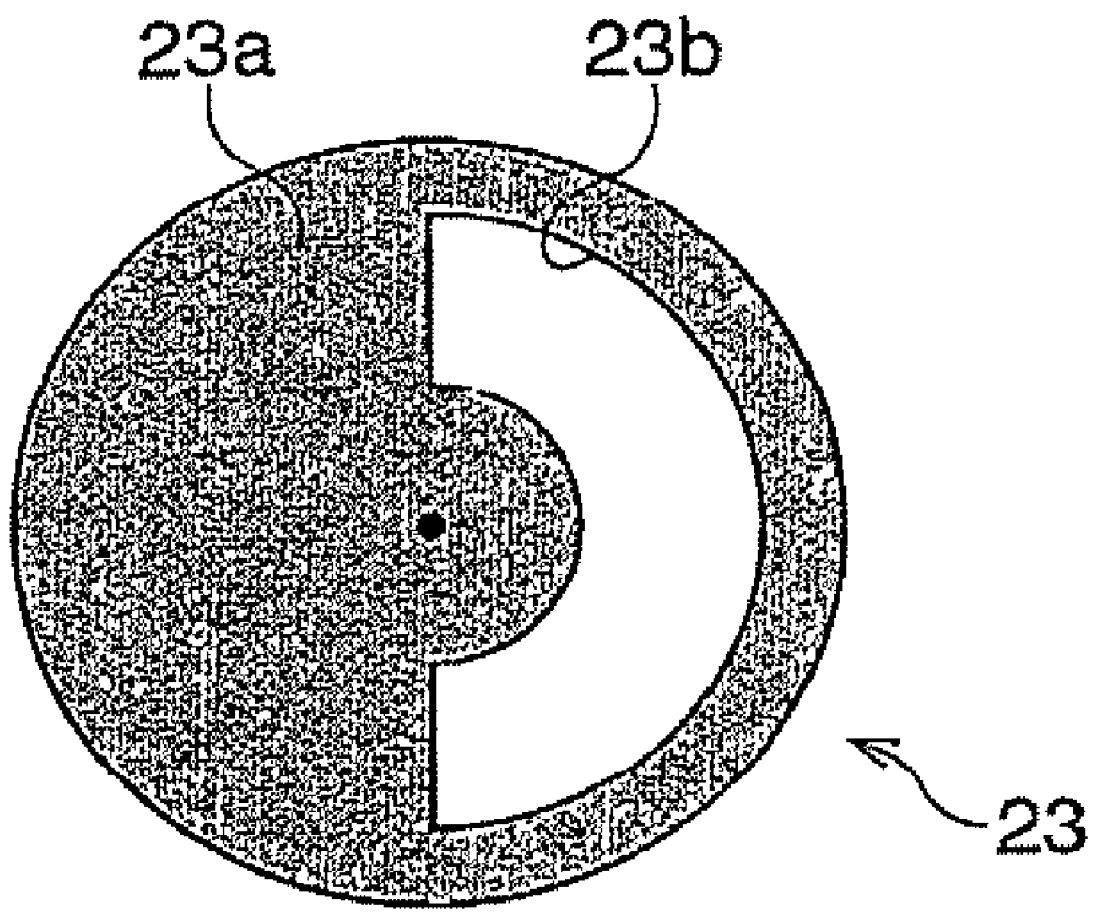
FIG. 2 is a schematic view of a rotary shutter.

As shown in FIG. 2, the rotary shutter 23 has a shading portion 23a and a light-transmitting portion 23b, which each form a half circumference. When the shading portion 23a is inserted into the passage of the white light W, the white light W is blocked out by the rotary shutter 23, so as not to be incident to the incident end 15B. On the other hand, when the light-transmitting portion 23b is inserted into the passage of the white light W, the white light W passes through the rotary shutter 23, so as to be incident to the incident end 15B. The rotary shutter 23 is rotated at a uniform speed by a second motor 35. The second motor 35 is driven by a second motor driving circuit 36.

The excitation-light source 31 is driven by a light driving circuit 34. Whether the excitation-light F is illuminated onto the object and the quantity of the excitation-light that is illuminated onto the object are adjusted by the light driving circuit 34.

The white light W or the excitation-light F, which is incident to the light guide 15, and which passes through the light guide 15, is illuminated onto the tissue (an object) in the organ from the output end 15 (namely, from the tip portion 11a). The white light W, which is illuminated from the tip portion 11a, is reflected off the object. The reflected white light is received at a photo-sensor area of the imaging device 14 via the objective lens 13, so that the imaging device 14 captures a normal image that is formed at the photo-sensor area from the reflected white light. On the other hand, when the excitation-light F is illuminated from the tip portion 11a onto the object, the object enters into an excited state and emits auto-fluorescence. The auto-fluorescence is received at the photo-sensor area via the objective lens 13, so that the imaging device 14 captures a fluorescent image that is formed at the photo-sensor area from the auto-fluorescence. Further, the excitation-light F that is reflected off the object is absorbed by the excitation-light cut filter 19, so that the excitation-light F is not incident to the imaging device 14.

The imaging device 14 generates image signals as analog signals corresponding to the normal image or the fluorescent image that is captured by the photo sensor area thereof. The imaging device 14 can be an interlaced CCD, for example, so that the imaging device 14 captures an odd-field image in an odd-field period, and captures an even-field image in an even-field period. The imaging device 14 is controlled by control signals that are input from the imaging device drive/control circuit 38. The imaging device 14 generates one-field image signals (the odd-field or even-field image signals) that correspond to the one-field image (the odd-field or even-field image), and that have a plurality of pixel signals, each pixel signal being composed of a luminance signal Y and color difference signals Cb and Cr (color signals). The one-field image signals are output on the monitor 46 as the display image after they undergo several image processing processes at an image processing block 50.

Figure 7:
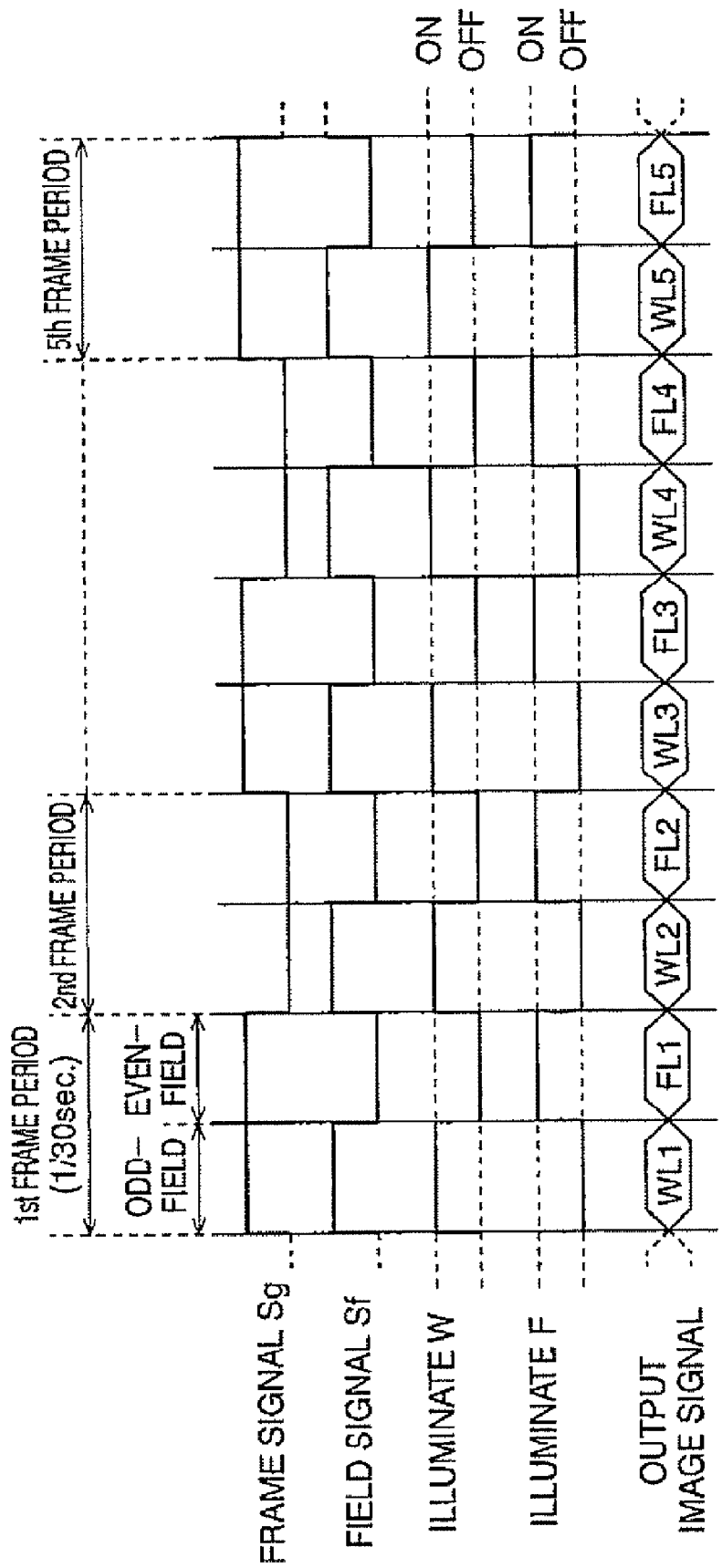
FIG. 7 is a timing chart showing the method of generation of image signals on an imaging device.

The timing controller 40 generates frame signals Sg and field signals Sf (see FIG. 7). The timing of driving each circuit in the video-processor 20 is controlled by the frame signals Sg and the field signals Sf.

Figure 3:
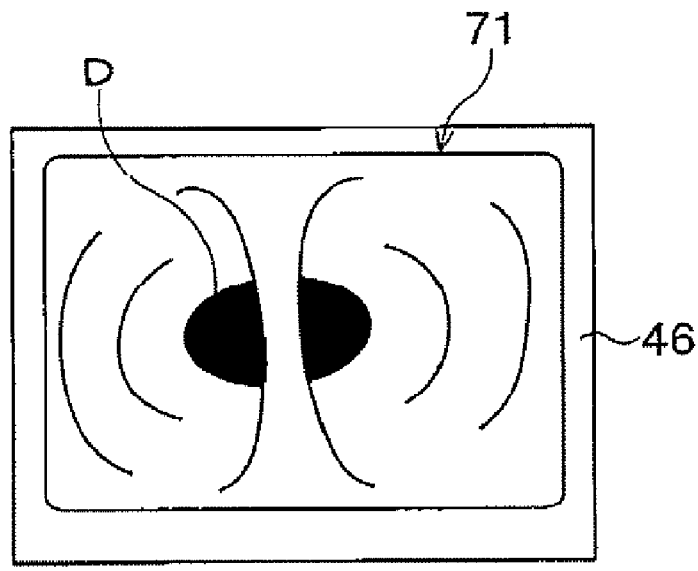
FIG. 3 is a schematic view showing a normal image which displayed on a monitor.

The video-processor 20 has a mode switch 37 and a level-set switch 61. In this embodiment, the electronic endoscope system 10 enters one selected mode that is selected among a plurality of modes according to the input at the mode switch 37. The display image that is displayed on the monitor 46 changes according to the selected mode. For example, when the selected mode is the normal imago mode, a normal image 71 is displayed on the monitor 46 as the display image, as shown in FIG. 3. The normal image 71 indicates the objects that are illuminated by the white light W. In the normal image 71, the tissue (the object) in the organ is shown by natural bright color based on the reflected white light W, and the lumen D (hollow portion) in the organ is shown by black or dark color, because the lumen D does not reflect the white light W.

Figure 4:
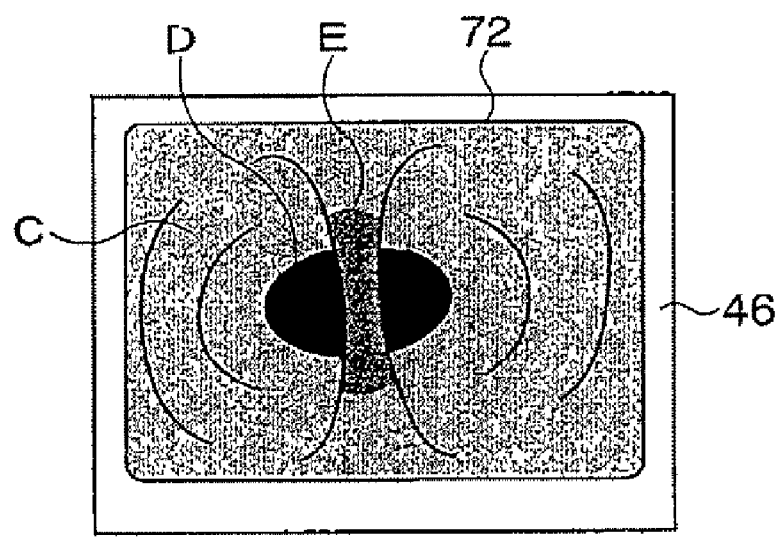
FIG. 4 is a schematic view showing a fluorescent image that is displayed on a monitor.

When the selected mode is the fluorescent image mode, a fluorescent image 72 is displayed on the monitor 46 as the display image, as shown in FIG. 4. The fluorescent image 72 is an image based on the auto-fluorescence emitted by the tissue that enters into an excited state by the excitation-light F. In the fluorescent image 72, the fluorescent emission by the abnormal tissue E is weaker than that of the normal tissue C; therefore, the abnormal tissue is identified according to the intensity of the fluorescent emission in the fluorescent image 72. However, the lumen D, which can not emit fluorescence, is relatively dark in the fluorescent image 72, similar to the abnormal tissue E; therefore, the lumen D is not distinguished from the abnormal tissue E if the fluorescent image 72 is referenced.

Figure 5:
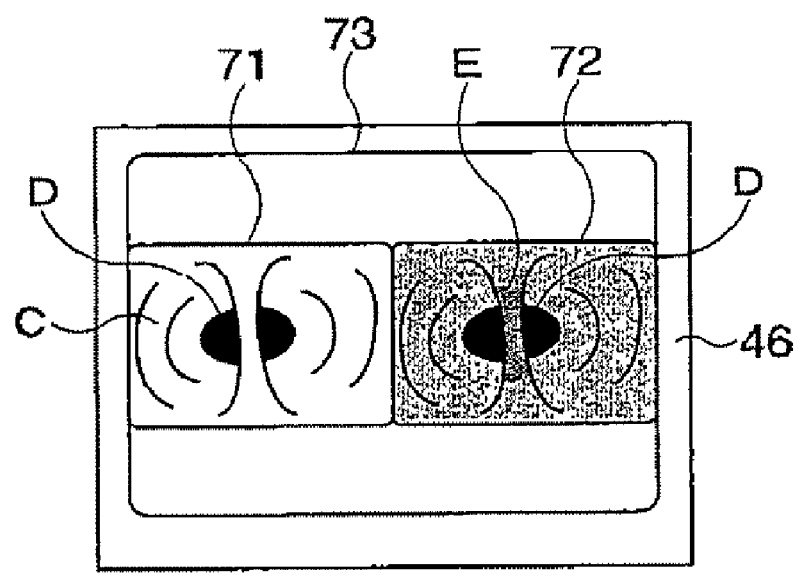
FIG. 5 is a schematic view showing a twin image that is displayed on a monitor.

When the selected mode is the twin mode, a twin image 73 is displayed on the monitor 46 as the display image, as shown in FIG. 5. The twin image 73 is composed of the normal image 71 and the fluorescent image 72 arranged sidewise.

Figure 6:
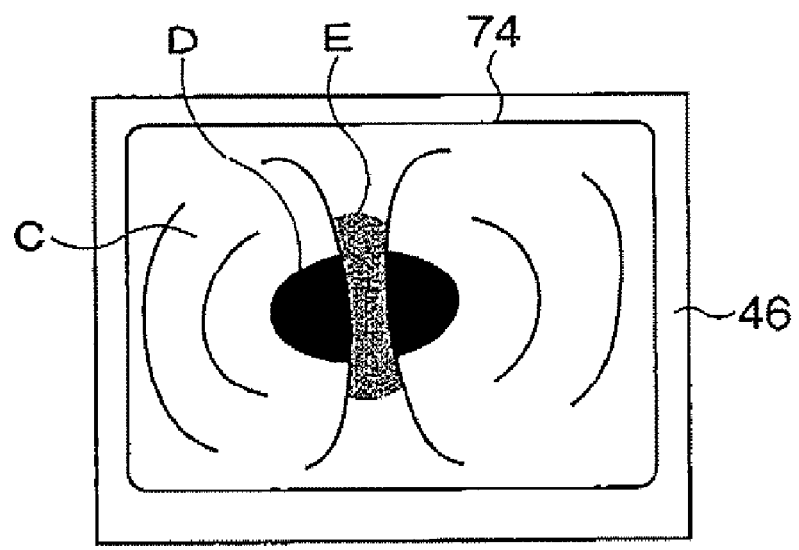
FIG. 6 is a schematic view showing a synthesized image that is displayed on a monitor.

When the selected mode is the synthesized image mode, a synthesized image 74 is displayed on the monitor 46 as the display image, as shown in FIG. 6. In the synthesized image 74, the color difference signals Cb and Cr of each pixel are determined to be the same signals as the color difference signals Cb and Cr of each pixel in the normal image 71, and the luminance signal Ys of each pixel is obtained by mixing the luminance signal Yw of each pixel in the normal image 71 and the luminance signal Yf in the fluorescent image 72 in a predetermined proportion.

The method for generation of a synthesized image is explained below in detail, using FIGS. 7-9. FIG. 7 is a timing chart showing the method of generation of the image signals on the imaging device 14 for five frame periods when the selected mode is the synthesized image mode. Further, the five frame periods are called "$1^{st}$-$5^{th}$ frame periods", respectively, hereinafter. Further, the method of generation of the image signals for frames periods other than the $1^{st}$-$5^{th}$ frame periods is the same as that for the $1^{st}$-$5^{th}$ frame periods. Furthermore, one-field image signals corresponding to the normal image and one-field image signals corresponding to the fluorescent image in the $n^{th}$ frame period are called "the normal image signals WLn" and "the fluorescent image signals FLn", respectively. Furthermore, the preceding frame period of the $1^{st}$ frame period is called to the $0^{th}$ frame period.

The frame signal Sg is output for the frame period in the odd-frame periods (the $1^{st}$, $3^{rd}$, and $5^{th}$ frame periods), and it is not output for the frame period in the even-frame periods (the $2^{nd}$ and $4^{th}$ frame periods). The field signal Sf is output for the first half-period (an odd-field period), but is not output for the second half-period (an even-field period), in every one frame period. For example, one frame period is 1/30 second long, so a half period is 1/60 second long.

The rotary shutter 23 is rotated based on the field frame signal Sf, so that the white light W that is emitted by the white light source 21 passes through the light-transmitting portion 23b for the odd-field period, but is blocked out by the shading portion 23a for the even-field period. The excitation-light source 31 is driven based on the field frame signal SE, so that the excitation-light F in not emitted by the excitation-light source 31 for the odd-field period, but is emitted for the even-field period. Due to this, the object is not illuminated by the excitation-light, but is illuminated by the white light W, for the odd-field period. Further, the object is not illuminated by the white light N, but is illuminated by the excitation-light F, for the even-field period. Namely, either the white light W or the excitation light F is illuminated onto the object alternately for each of the two field periods, which continue interleavingly.

The imaging device 14 is controlled by the field signal Sf. The imaging device 14 stores the electrical charge corresponding to either the normal image or the fluorescent image that is formed on the photo-sensor area. Then, the imaging device 14 converts the stored electrical charge to either the normal image signals WLn or the fluorescent image signals FLn in each field period.

In the odd-field period, the white light W is illuminated onto the object, and the imaging device 14 captures the normal image based on the white light W, which is reflected off the object. Therefore, the normal image signals WLn corresponding to the normal image are generated at the imaging device 14, and are input to the image processing block 50, in the odd-field period.

On the other hand, the excitation-light F is illuminated onto the object, and the imaging device 14 captures the fluorescent image based on the auto-fluorescence that is emitted by the object. Therefore, the fluorescent image signals FLn, corresponding to the fluorescent image, are generated at the imaging device 14, and are input to the image processing block 50, in the even-field period. Namely, either the normal image signals WLn or the fluorescent image signals FLn are alternately generated and are output in each of two field periods on every frame.

Figure 8:
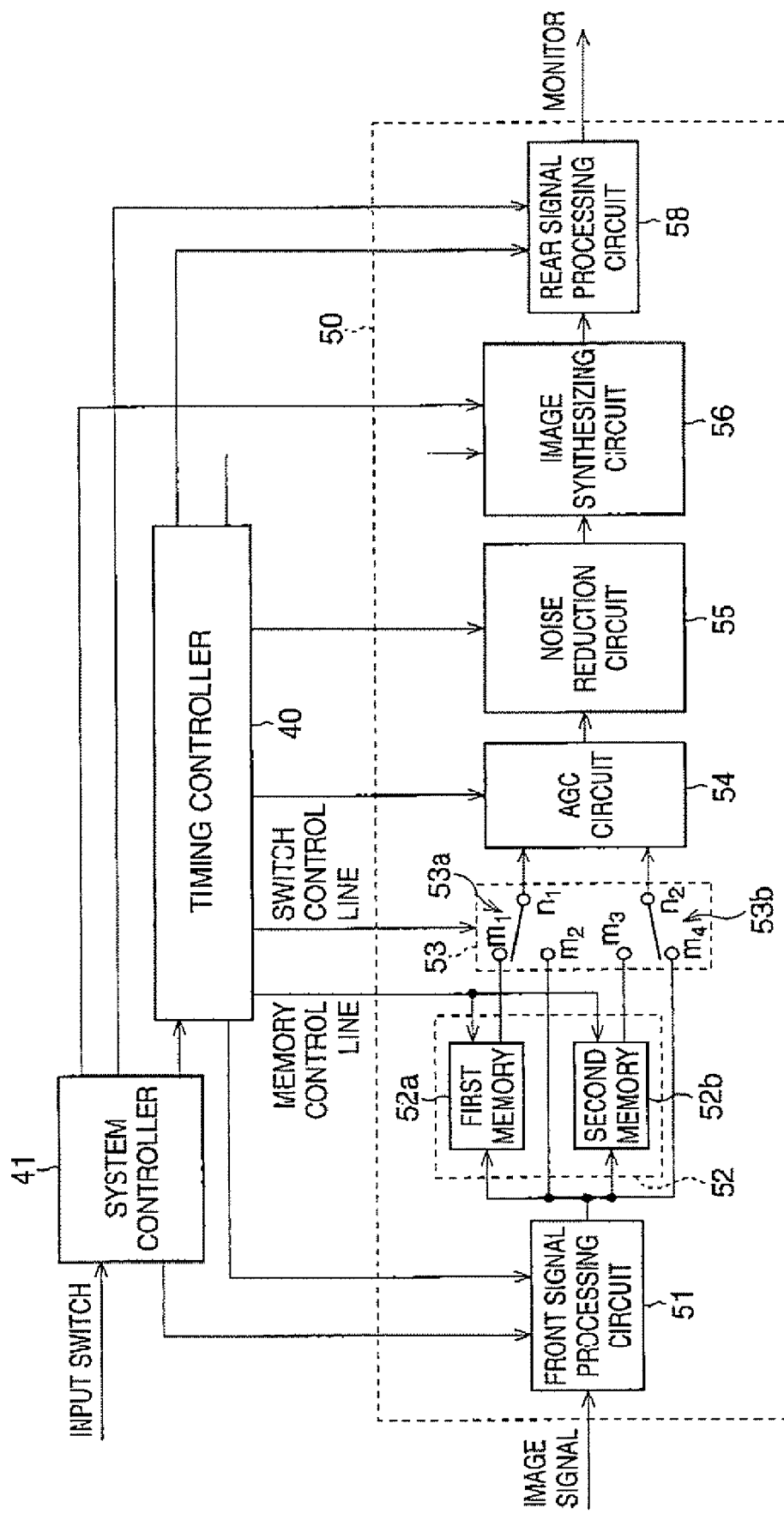
FIG. 8 is a circuit diagram showing the image processing block.

FIG. 8 is a circuit diagram showing the image processing block 50. The normal image signals WLn or the fluorescent image signals FLn are input to a front signal processing circuit 51. At the front signal processing circuit 51, the image signals WLn and FLn undergo several necessary image processes, including color adjustment, and are converted to digital image signals. The normal image signals WLn that have been converted to digital signals are transformed into pseudo-frames of image signals at a pseudo-framing block 52 and a switch circuit 53. Similarly, the fluorescent image signals FLn that have been converted to digital signals are transformed into pseudo-frames of image signals.

The pseudo-framing block 52 has first and second memories 52a and 52b, which are connected to the timing controller 40 by a memory control line. The timing of storing the image signals therein and the timing or reading-out the image signals therefrom are controlled by the timing controller 40.

The switch circuit 53 has a first switch 53a that is composed of input terminals m1 and m2 and an output terminal n1, and a second switch 53b that is composed of input terminals m3 and m4 and an output terminal n2.

The front signal processing circuit 51 has four output terminals. The two of the four output terminals are respectively connected to the first and second memories 52a and 52b. The first and second memories 52a and 52b are respectively connected to the input terminals m1 and m3. The other two terminals in the four output terminals are directly connected to the input terminals m2 and m4 respectively. The first and second switches 53a and 53b are connected to the timing controller 40 by a switch control line. The switch timing of the first and second switches 53a and 53b is controlled by the timing controller 40.

Figure 9:
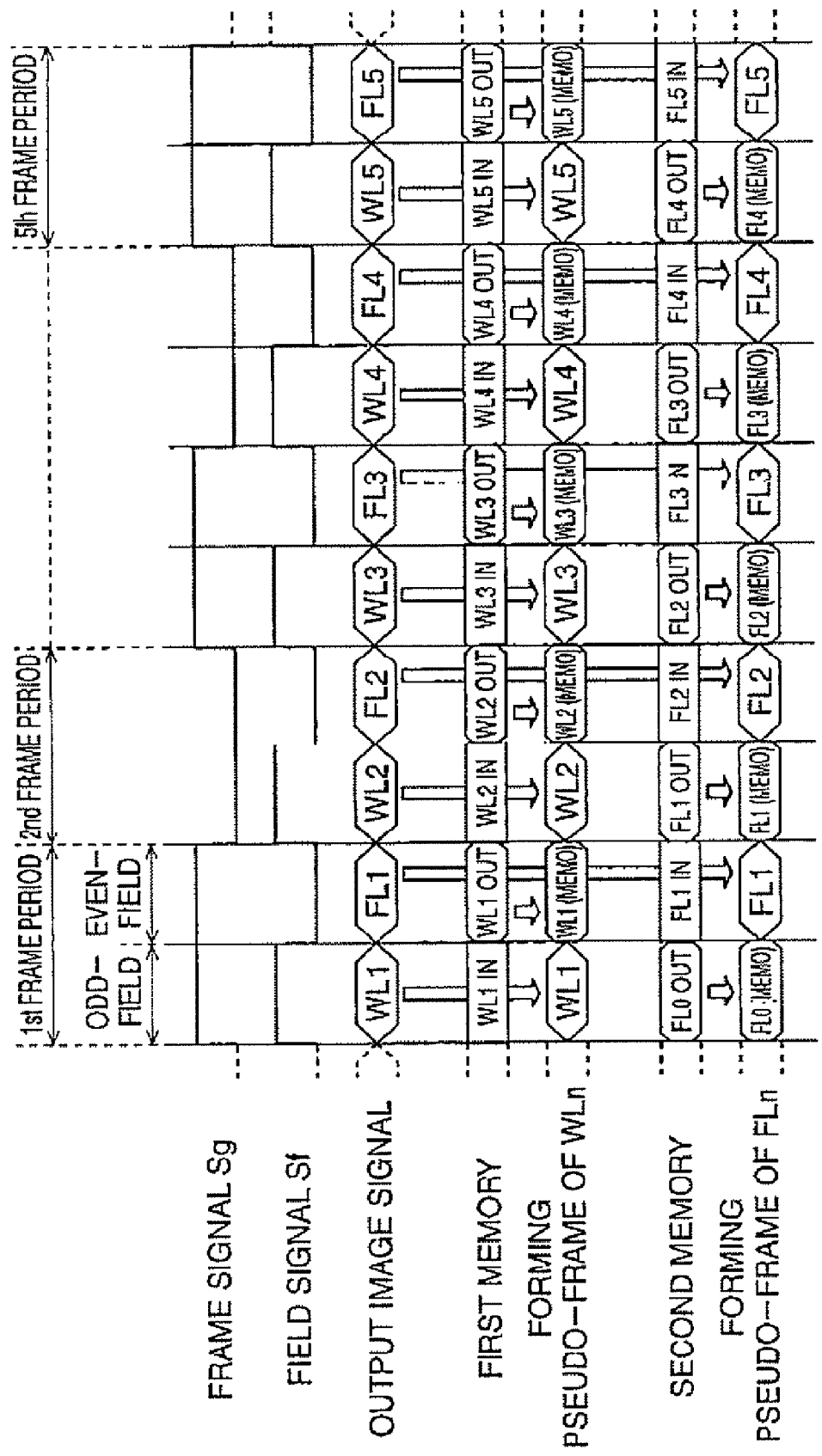
FIG. 9 is a timing chart showing the method for forming pseudo-frames for five frame periods.

FIG. 9 is a timing chart showing the method for forming pseudo-frames for five frame periods. The method of forming one pseudo-frame of the normal image signal WLn in the first frame period is explained below, using FIGS. 8 and 9. Further, the method for forming one pseudo-frame of the normal image signals in the other frame periods is the same as that for the first frame; therefore, these explanations are omitted below.

In the odd-field period, the first switch 53a causes the input terminal m2 to connect to the output terminal n1. Then, the normal image signals WL1, which are generated on the imaging device 14, are input to an AGC (Auto Gain Controller) circuit 54 from the front signal processing circuit 51 via input terminal m2 and output terminal n1, not via the first memory 52a. Further, the normal image signals WL1 are also input to the first memory 52a from the imaging device 14, and are memorized therein in the odd-field period.

On the other hand, in the even-field period, the first switch 53a causes the input terminal m1 to connect to the output terminal n1. Then, the normal image signals WL1, which have been memorized in the first memory 52a in the odd-field period, are read out from the first memory 52a. The read-out normal image signals WL1 are input to ACC circuit 54 via the input terminal m1 and the output terminal n1. Namely, the normal image signals WL1, which have been memorized in the first memory 52a, are read-out as the normal image signals that are assumed to be generated in the even-field period, because the normal image signal is not generated by the imaging device 14 for the even-field period.

As described above, in the first frame period, one pseudo-frame of the normal image signal is composed of one field of normal image signals WL1 (one-field image signals) generated on the imaging device 14 and one field of normal image signals WL1 (one-field image signals) read from the first memory 52a. Then, the resulting pseudo-frame of the normal image signals are input to the AGC circuit 54. Further, the normal image signals WL1 that are input to the AGC circuit 54 in the odd-field period or in the even-field period are input to the image synthesizing circuit 56 through the noise reduction circuit 55 in the odd field period or in the even-field period, respectively, as described below.

Next, the method for forming one pseudo-frame of the fluorescent image in the first frame period is explained, using FIGS. 8 and 9. Further, the method for forming one pseudo-frame of the fluorescent image signals in the other frame periods is the same as that for the first frame; therefore, these explanations are omitted below.

In the odd-field period, the second switch 53b causes the input terminal m3 to connect to the output terminal n2. Further, the second memory 52b memorizes the fluorescent image signals FL0 that have been generated in the even-field period of the $0^{th}$ frame period. Therefore, the fluorescent image signals FL0 are read out front the second memory 52b, and are input to the AGC circuit 54 as the fluorescent image signals that are assumed to be generated in the odd-field period, because the imaging device 14 does not generate the fluorescent image signals for the odd-field period.

In the even-field period, the second switch 53b causes the input terminal m4 to connect to the output terminal n2. Then, the fluorescent image signals FL1 that are generated in the even-field period are input to the AGC circuit 54 from the front signal processing circuit 51 via input terminal m4 and output terminal n2, not via the second memory 52a. The fluorescent image signals FL1 are also input to the second memory 52b, and are memorized therein in this period. Further, the fluorescent image signals FL1 that are memorized in the second memory 52b are read out in the odd-field period of the second frame period.

As described above, in the first frame period, one pseudo-frame of the fluorescent image signals is composed of one field of the fluorescent image signals FL0 (one-field image signals) read from the second memory 52b and one field of the fluorescent image signals FL1 (one-field image signals) generated on the imaging device 14. The resulting pseudo-frame of the fluorescent image signals are input to the AGC circuit 54. Further, the fluorescent image signals FL0 or FL1 that are input to the AGC circuit 54 in the odd-field period or in the even-field period are input to the image synthesizing circuit 56 through the noise reduction circuit 55 in the odd-field period or in the even-field period, respectively, as described below.

Next, the method for processing image signals that have been transformed into pseudo-frames of image signals in the odd-field period of the first frame period is explained below, using FIG. 8. Further, the method for processing the pseudo-frames of image signals in the other field periods is the same as that in the odd-field period of the first frame; therefore, these explanations are omitted below.

At the AGC circuit 54, the gain adjustment is carried out so that a luminance level of the normal image signals WL1 coincides with that of the fluorescent image signals FLO. Namely, both the average of luminance values (luminance signals) of pixel signals in the normal image signals WL1 and the average of luminance values (luminance signals) of pixel signals in the fluorescent image signals FLO are calculated at first. Next, the gain of the luminance signals in the fluorescent image signals is adjusted. Namely, each of the luminance values (luminance signals) of pixel signals in the fluorescent image signals FLO is multiplied by a coefficient, so that the average of the luminance values in the fluorescent image signals FLO coincides with the average of the luminance values in the normal image signals WL1. Generally, the luminance value of the fluorescent image is lower than that of the normal image, so that the coefficient is determined to be greater than 1, and the gain of the luminance signals in the fluorescent image signals FLO is increased normally.

The normal image signals WL1 and the fluorescent image signals FLO are input to the noise reduction circuit 55 after gain adjustment. Noise in the fluorescent image signals FLO must increase at the AGC circuit 54 because the gain of the fluorescent image signals FLO is increased thereat. Therefore, the noise in the fluorescent image signals FLO is reduced by the noise reduction circuit 55, which can be, for example a median filter. After noise reduction, the fluorescent image signals FLO are input to an image synthesizing circuit 56. On the other hand, noise in the normal image signals WL1 does not increase at the AGC circuit 54 because the gain of the normal image signals WL1 is not increased thereat. Therefore, the normal image signals WL1, whose noise is not reduced by the noise reduction circuit 55, are input to the image synthesizing circuit 56.

At the image synthesizing circuit 56, the normal image signals WL1 are synthesized with the fluorescent image signals FLO into synthesized image signals. Color difference signals Cb and Cr of each pixel signal in the synthesized image signals are determined to be the same signals as the color difference signals Cb and Cr of each pixel signal in the normal image signal WL1.

On the other hand, a luminance signal Ys of each pixel signal in the synthesized image signals is generated by mixing a luminance signal Yw of each pixel signal in the normal image signals WL1 and a luminance signal Yf of each pixel signal in the fluorescent image signal FLO in a predetermined proportion. Namely, the luminance signal Ys in each pixel signal in the synthesized image signals is generated as shown in formula (1).

$$Ys = \alpha \times Yw + \beta \times Yf$$

$$(\alpha = \beta 1, \alpha \geq 0, \beta \geq 0) \qquad (1)$$

According to formula (1), the luminance level of the synthesized image signals is kept to the coinciding luminance level that is adjusted at the AGC circuit 54, because $\alpha + \beta$ is defined to be 1. The values of $\alpha$ and $\beta$ can be act by an input switch from the level-set switch 61.

The synthesized image signals that are generated at the image synthesizing circuit 56 are input to a rear signal processing circuit 58, and are converted to analog signals thereat. The analog signals of the synthesized image signals are displayed as the synthesized image 74 on the monitor 46.

As shown in FIG. 6, the normal tissue C can reflect white light W when the white light W is illuminated onto the normal tissue C. In addition to this, the normal tissue C can emit the strong fluorescence when the excitation-light F is illuminated onto it. Therefore, the normal tissue C is indicated as a relatively bright portion in the synthesized image 74.

On the other hand, the abnormal tissue E can reflect white light W when the white light W is illuminated onto the normal tissue C, similarly to with the normal tissue C. However, the abnormal tissue E cannot emit strong fluorescence when the excitation-light F is illuminated onto it. Therefore, the abnormal tissue E is indicated as a relatively dark portion in the synthesized image 74. Due to this, the abnormal tissue E is distinguished from the normal tissue C in the synthesized image 74.

The luminance value of the synthesized image 74 not only refers to the luminance value of the fluorescent image but also) refers to the luminance value of the normal image. Therefore, the abnormal tissue E is brighter than the lumen D in the synthesized image 74, so that the abnormal tissue E is also distinguished from the lumen D in the synthesized image 74, because the lumen D does not emit the auto-fluorescence and does not reflect the white light, either.

The color difference signals Cb and Cr in the synthesized image signals are the same as those in the normal image 71, so that the color reproductivity of the synthesized image 74 is as good as that of the normal image 71.

Incidentally, the luminance of the bleeding part in the synthesized image 74 is low, similar to that of the abnormal tissue E, because the bleeding part can not emit strong fluorescence. Therefore, the bleeding part is not distinguished from the abnormal tissue E it only the luminance values in the synthesized image 74 are referenced.

However, the bleeding part is indicated as pure red, but the abnormal tissue E is indicated as the normal color, similar to the normal tissue C. Therefore, the bleeding part is distinguished from the abnormal tissue E in the synthesized image 74.

Furthermore, since the value of $\alpha$ and $\beta$ are set according to the user's demand using the level-set switch 61, the user can decide in what proportion the fluorescent image is synthesized into the resulting image.

Next, the display image is explained below, when the selected mode is set to a mode other than the synthesized image mode. When the selected mode is the twin mode, either the white light W or the excitation-light F is illuminated alternately in each of two field periods in each frame period, similarly to with the image synthesized mode. Therefore, the object is illuminated by the white light W in the odd-field period, so that the normal object image signals are generated in the odd-field period. On the other hand, the object is illuminated by the excitation-light F in the even-field period, so that the fluorescent image signals are generated in the odd-field period. The normal image signals and the fluorescent image signals, which are generated alternately, are synthesized into the twin image 73.

Next, the method for generation of the twin image 73 is explained. In the odd-field period of the odd-frame period, the normal image signals WL1, while are output from the imaging device 14, are memorized into the first memory 52a. In the even-field period of the odd-frame period, the fluorescent image signals FLn, which are output from the imaging device 14 as described above, are memorized into the first memory 52a.

In the odd-field period of the even-frame period, the normal image signals WLn, which are output from the imaging device 14, are memorized into the second memory 52b. In the even-field period of the even-frame period, the fluorescent image signals FLn, which are output from the imaging device 14 as described above, are memorized into the second memory 52b.

Both the normal image signals WLn and the fluorescent image signals FLn that have been memorized into the first memory 52a in the odd-frame period are read out from the first memory 52a in the following even-frame period. When the image signals are read out, one line of the normal image signals WLn and one line of the fluorescent image signals FLn are alternately and continuously read out, and are compressed to ½ line of the image signals. The ½ line of the normal image signals WLn is synthesized with the ½ line of the fluorescent image signals FLn, so as to form one line image signals composed of ½ line of the normal image signals WLn and ½ line of the fluorescent image signals FLn. The reading-out and synthesization continue so that the twin image signals corresponding to the twin image 73 that is composed of the normal image and the fluorescent image arranged sidewise are generated, as shown in FIG. 5.

Similarly, the normal image signals WLn and the fluorescent image signals FLn that are memorized into the second memory 52b in the even-field period are read out and synthesized into the twin image signals corresponding to the twin image 73.

The twin image signals are output to the monitor 46 as the twin image 73 through the AGC circuit 54, the noise reduction circuit 55, the image synthesizing circuit 58, and the rear signal processing circuit 58. In this case, the AGC circuit 54 adjusts the gain of the twin image signals, and the noise reduction circuit 55 reduces the noise of the twin image signals, but the image synthesizing circuit 58 does not process the twin image signal. Further, the rear signal processing circuit 58 converts the twin image signals to analog signals.

Next, the case when the selected mode is the normal mode is explained. In this case, the white light W is always illuminated onto the object, so that the imaging device 14 generates the normal image signals in both odd-field and even-field periods. Therefore, the normal image signals are processed according to a predetermined image processing process without transforming into the pseudo-frames of image signals at the pseudo-framing block 52, and are output to the monitor 46 as a normal image.

Similarly, the excitation-light F is always illuminated onto the object, and the fluorescent image 72 is displayed on the monitor 46 when the selected mode is the fluorescent mode.

As described above, the image processing block 50 can generate the normal image 71, the fluorescent image 72, the twin image 73, and the synthesized image 74 without complicated circuitry.

Further, in this embodiment, the normal image is captured when the white light W (namely, the normal light) is illuminated onto the object. However, visible light other than the white light WL can be used as the normal light that is illuminated onto the object, but white light or visible light that can be substantially regarded as white light is preferred.

Further, the gain adjustment at the AGC circuit 54 can be carried out by methods other than the method described above. For example, each of the luminance values (luminance signals) of pixel signals in the fluorescent image signals FLO can be multiplied by a coefficient, so that the highest luminance value of all pixel signals in the normal image signals WL1 is coincides with that in the fluorescent image signals FLO in order to have the luminance level of the normal image signals WL1 coincide with that of the fluorescent image signals FLO. However, this method does not seem to carry out the gain adjustment more accurately than the method described above, because it is possible that the luminance value of the noise is the highest luminance value in the fluorescent image or in the normal image.

Furthermore, in this embodiment, the color difference signals Cb and Cr are used as the color signals, but other types of the color difference signals can be used as the color signals; for example, the color difference signals (U, V), or the color difference signals (a, b).

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2005-263942 (filed on Sep. 12, 2005), which is expressly incorporated herein, by reference, in its entirety.

The invention claimed is:

1. An electronic endoscope system, comprising:
    a video-scope;
        an illumination apparatus that illuminates a normal light and an excitation-light from said video-scope onto an object, said normal light reflected from the object, and said excitation-light causing the object to enter into an excited state, so that the object emits fluorescence;
        an imaging device that is provided on said video-scope, and that receives the reflected normal light and the fluorescence, so as to capture a normal image and a fluorescent image, respectively; and
        an image synthesizing processor that synthesizes said normal image and said fluorescent image into a synthesized image, a color difference signal of said synthesized image being the same as a color difference signal of said normal image, and a luminance signal of said synthesized image Ys being obtained by mixing a luminance signal of said normal image Yw and a luminance signal of said fluorescent image Yf in accordance with the relationship: $Ys = \alpha \times Yw + \beta \times Yf$ where $\alpha + \beta = 1$, $\alpha \geq 0$, $\beta \geq 0$ and where $\alpha$ and $\beta$ are settable by a manually operable input switch.

2. An electronic endoscope system according to claim 1, further comprising:
    a gain adjustment processor that adjusts a gain of the luminance signal of at least one of said normal image and said fluorescent image, so that the luminance level of said normal image coincides with the luminance level of said fluorescent image,
    wherein the luminance level of said synthesized image is maintained at the coinciding luminance level.

3. An electronic endoscope system according to claim 2, wherein said gain adjustment processor adjusts said gain of said luminance signal so that an average of a luminance value of said normal image coincides with an average of a luminance value of said fluorescent image.

4. An electronic endoscope system according to claim 1, wherein said illumination apparatus illuminates said normal light for a predetermined period, and said excitation-light for another predetermined period; and
    said imaging device captures said normal image in said predetermined period, and said fluorescent image in said another predetermined period.

5. An electronic endoscope system according to claim 4, wherein said illumination apparatus alternately illuminates either said normal light or said excitation-light in each of two regular periods, so that said imaging device captures either said normal image or said fluorescent image alternately in each of two regular periods, and
    said image synthesizing processor synthesizes said normal image that is captured in one regular period of said two regular periods and said fluorescent image that is captured in the succeeding or the preceding period of said one regular period.

6. An electronic endoscope system according to claim 5, wherein said regular period is a one-field period.

7. An electronic endoscope system according to claim 5, wherein normal image signals corresponding to said normal image that are captured in said one regular period are input to said image synthesizing processor in said one regular period, and also in the regular period succeeding said one regular period,
    fluorescent image signals corresponding to said fluorescent image that are captured in the other regular period of said two regular periods are input to said image synthesizing processor in the other regular period, and also in the period succeeding the other regular period, and
    said image synthesizing processor synthesizes said normal image signals and said fluorescent image signals, which are input to the image synthesizing processor in the same regular period.

8. An electronic endoscope system, comprising:
    a video-scope;
    an illumination apparatus that transmits a normal light and an excitation light from said video-scope onto an object, said normal light being reflected from the object, and said excitation light causing the object to enter into an excited state, so that the object emits fluorescence;
    an imaging device that is provided on the video-scope, and that receives the reflected normal light and the fluorescence, so as to capture a normal image and a fluorescent image, respectively; and
    an image synthesizing processor that synthesizes said normal image and said fluorescent image into a synthesized image, a color difference signal of said synthesized image being the same as a color difference signal of said normal image, and the luminance signal of said synthesized image being obtained by mixing a luminance signal of said normal image and a luminance signal of said fluorescent image in predetermined proportions, wherein the predetermined proportions are selectively settable via a manually operable input switch.

9. The electronic endoscope system according to claim 8, further comprising a gain adjustment processor that adjusts a gain of the luminance signal of at least one of said normal image and said fluorescent image, so that the luminance level of said normal image coincides with the luminance level of said fluorescent image, wherein the luminance level of said synthesized image is maintained at the coinciding luminance level.

10. The electronic endoscope system according to claim 9, wherein said gain adjustment processor adjusts said gain of said luminance signal so that an average of a luminance value of said normal image coincides with an average of a luminance value of said fluorescent image.

11. The electronic endoscope system according to claim 8, wherein said illumination apparatus illuminates said normal light for a predetermined time period, and said excitation light for another predetermined time period; and said imaging device captures said normal image in said predetermined time period, and captures said fluorescent image in said another predetermined time period.

12. The electronic endoscope system according to claim 11, wherein said illumination apparatus alternately illuminates either of said normal light or said excitation light in each of two regular periods that alternate continuously, so that said imaging device alternately captures either said normal image or said fluorescent image in each of the two regular periods, and said image synthesizing processor synthesizes said normal image that is captured in one regular period of said two regular periods and said fluorescent image that is captured in the succeeding or the preceding period of said one regular period.

13. The electronic endoscope system according to claim 12, wherein said regular period is a one field period.

14. The electronic endoscope system according to claim 12, wherein normal image signals corresponding to said normal image that are captured in said one regular period are input to said image synthesizing processor in said one regular period and in the regular period succeeding said one regular period, fluorescent image signals corresponding to said fluorescent image that are captured in the other regular period of said two regular periods are input to said image synthesizing processor in the other regular period, and in the period succeeding the other regular period; and said image synthesizing processor synthesizes said normal image signals and said fluorescent image signals, which are input to the image synthesizing processor in the same regular period.

\* \* \* \* \*